US00PP16677P2

(12) United States Plant Patent
Boeder

(10) Patent No.: US PP16,677 P2
(45) Date of Patent: Jun. 20, 2006

(54) ***CHRYSANTHEMUM* PLANT NAMED 'CRETE'**

(50) Latin Name: *Chrysanthemum morifolium*
Varietal Denomination: Crete

(75) Inventor: Mark Roland Boeder, The Hague (NL)

(73) Assignee: Chrysanthemum Breeders Association N.V. (NL)

( * ) Notice: Subject to any disclaimer, the term of this patent is extended or adjusted under 35 U.S.C. 154(b) by 75 days.

(21) Appl. No.: 11/020,134

(22) Filed: Dec. 27, 2004

(51) Int. Cl.
*A01H 5/00* (2006.01)

(52) U.S. Cl. ..... Plt./288

(58) Field of Classification Search ..... Plt./288
See application file for complete search history.

*Primary Examiner*—Anne Marie Grunberg
*Assistant Examiner*—Annette H Para
(74) *Attorney, Agent, or Firm*—Steptoe & Johnson LLP

(57) ABSTRACT

A *chrysanthemum* plant named 'Crete' characterized by its small sized blooms with white ray florets and good branching; natural season flower date September 13–20; blooming for a period of 4 weeks.

3 Drawing Sheets

BACKGROUND OF THE INVENTION

'Crete' is a product of a breeding and selection program for outdoor pot mums (garden mums) which had the objective of creating new *chrysanthemum* cultivars with a decorative type flower, a natural season flower date around September 13–20; blooming for a period of 4 weeks. The new plant of the present invention comprises a new and distinct cultivar of *Chrysanthemum* plant 'Crete' is a seedling resulting from a crossing program, which was set up by a previous breeder, and which records are unknown to the inventor. The new and distinct cultivar was discovered and selected as one flowering plant by Mark Roland Boeder on a cultivated field in Rijsenhout, The Netherlans in 2001. The first act of asexual production of 'Crete' was accomplished when vegetative cuttings were taken from the initial selection in 2001 in a controlled environment in Rijsenhout, The Netherlans, and propagated further at this location. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
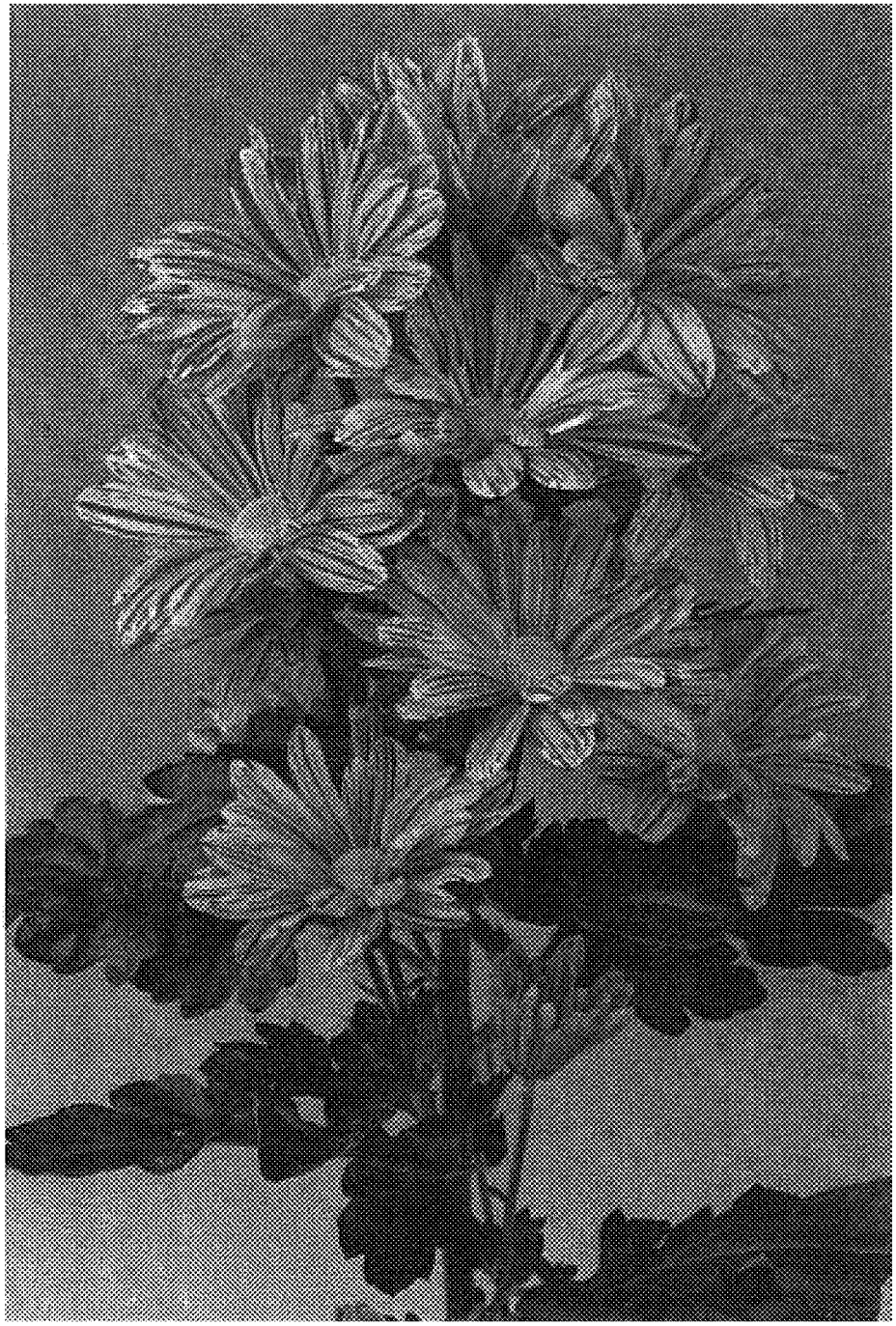
FIG. 1 shows a plant of the cultivar in full bloom.
Figure 2:
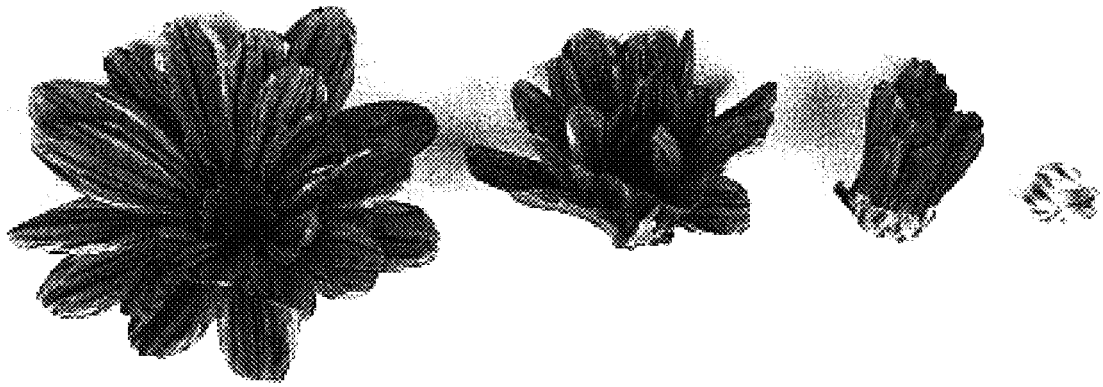
FIG. 2 shows the various stages of bloom of the new cultivar.
Figure 3:
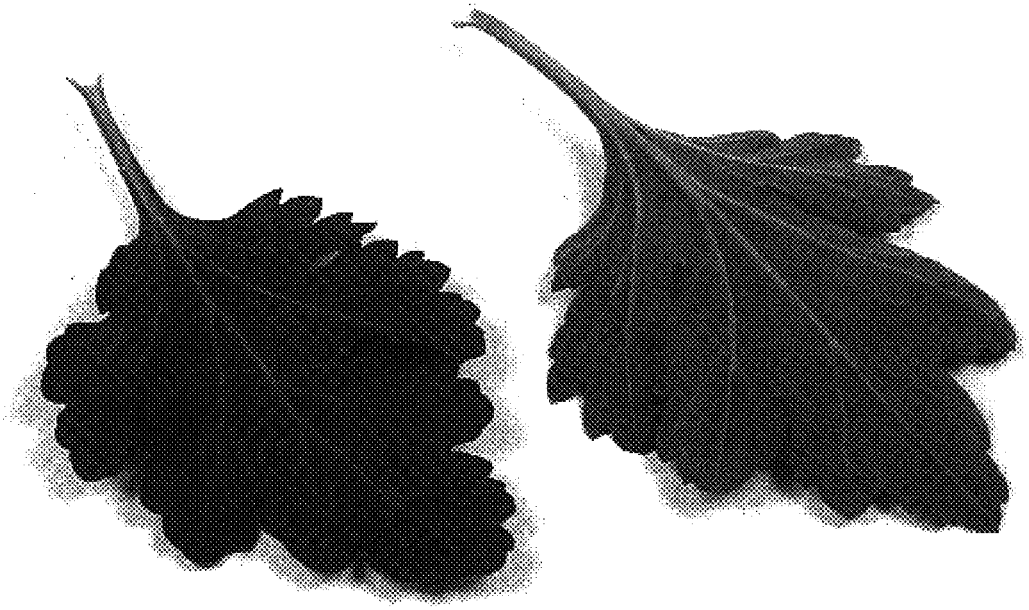
FIG. 3 shows the foliage of the new cultivar.

This new variety of *chrysanthemum* is of the botanical classification *Chrysanthemum morifolium L.* The observations and measurements were gathered from plants grown out door in Rijsenhout, The Netherlans under natural day length and temperature and planted week 24 in 2004. The natural blooming date of this crop was September 13–20 (week 38). The average height of the plants was 25 cms. No growth retardants were used. No tests were done on disease or insect resistance or susceptibility. No tests were done on cold or drought tolerance. This new variety produces small sized blooms with white ray florets and a cream center blooming for a period of 4 weeks.

From the cultivars known to inventor the most similar existing cultivar in comparison to 'Crete' is 'Unicorn' (U.S. Plant Pat. No. 14,697). When 'Unicorn' and 'Crete' are being compared the following similarities and differences are noticed: Both varieties have small white decorative type blooms. The differences of 'Unicorn' and 'Crete' are (1). Plant vigor. The plants of 'Unicorn' are more vigorous than those of 'Crete'. (2). Bloom size. The flowers of 'Unicorn' are larger than those of 'Crete'.

The following is a description of the plant and characteristics that distinguish 'Crete' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of *chrysanthemum* plant 'Crete'

| | |
|---|---|
| Bud | |
| Size | Small; cross-section 0.3 cm, height 0.2 cm |
| Outside Color | Yellow-green 145D |
| Involucral bracts | 2 rows, length 7 mm, width 3 mm |
| Involucral bracts among disc-florets | Not present |
| Involucral bracts color | Green 138B |
| Bloom | |
| Type | Decorative |
| Height | 1 cm |
| Size | Small |
| Fully Expanded | 3 cm |
| Peduncle length | 4.5 cm |
| Peduncle color | Greyed-green 194A–Green 138B |
| Number of blooms per branch | Approx. 4–5 blooms per branch |
| Performance on the plant | 4 weeks |
| Seeds | Produced in small quantities, |

TABLE 1-continued

| Botanical Description of *chrysanthemum* plant 'Crete' | |
|---|---|
| | ovate grey-brown 199A, 1½ mm in length. |
| Fragrance | Typical *chrysanthemum,* slightly |
| Color | |
| Center of the flower | Immature Yellow 2B<br>Mature Yellow 13A |
| Color of upper surface of the ray-florets | Yellow-white 158D |
| Color of the lower surface of the ray-florets | White 155D |
| Tonality from Distance | A garden mum with white flowers and a cream disc |
| Discoloration to color | White 155D |
| Ray florets | |
| Texture | Upper and under side smooth |
| Number | 180–200 |
| Cross-section | Flat |
| Longitudinal axis of majority | Straight |
| Length of corolla tube | 0.3 cm |
| Ray-floret margin | Entire |
| Ray-floret length | 1.6 cm |
| Ray-floret width | 0.3 cm |
| Ratio length/width | High |
| Shape of tip | Pointed |
| Disc florets | |
| Disc diameter | 0.1 cm |
| Distribution of disc florets | Few, only visible in mature stage |
| Shape | Tubular |
| Color | Yellow 11D |
| Receptacle shape | Conical raised |
| Reproductive Organs | |
| Stamen | present in disc florets only |
| Stamen color | Yellow-green 144A |
| Pollen | Present |
| Pollen color | Yellow 7A |
| Styles | Thin |
| Style color | Yellow 13A |
| Style Length | 3 mm |
| Stigma color | Yellow-green 144A |
| Stigma Width | 1 mm |
| Ovaries | Enclosed in calyx |
| Plant | |
| Form | Grown as a spray type potmum, outdoor mounded and round |
| Growth habit | Spherical shape |
| Growth rate | Low |
| Height | 25 cm |
| Width | 36 cm |
| Stem Color | Grey-brown 199B |
| Stem Strength | Medium |

TABLE 1-continued

| Botanical Description of *chrysanthemum* plant 'Crete' | |
|---|---|
| Stem Brittleness | Not brittle |
| Stem Anthocyanin Coloration | Absent |
| Internode length | 1.5–2 cm |
| Length of lateral branch | From top to bottom 10 cm |
| Lateral branch color | Yellow-green 147C |
| Lateral branch, attachment | Weak |
| Branching (average number of lateral branches) | Good with 8–10 breaks after pinching |
| Natural season blooming date | September 13–20 |
| Foliage | |
| Leaf color | Upper side Green 139A–139B<br>Lower side Green 136C–139C |
| Color midvein | Upper side Yellow-green 147D<br>Lower side Yellow-green 147D |
| Size | Small.; length 3 cm, width 1–3 cm |
| Quantity (number per lateral branch) | 15 |
| Shape | Obovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Obtuse |
| Apex | Mucronulate |
| Petiole length | 0.5 cm |
| Petiole color | Yellow-green 147D |

TABLE 2

| Differences with the comparison varieties | | |
|---|---|---|
| | 'Crete' | 'Unicorn' |
| Bloom type | Decorative | Decorative |
| Bloom size | 3 cm | 3.5–4 cm |
| Color upper side ray-florets | Yellow-white 158D | White 155D |
| Growth rate | Low | High |

I claim:

1. A new and distinct variety of *chrysanthemum* plant as described and illustrated.

* * * * *